(12) United States Patent
Algawi et al.

(10) Patent No.: US 10,874,416 B2
(45) Date of Patent: Dec. 29, 2020

(54) SURGICAL CUTTING INSTRUMENT WITH EXTENDED BLADES

(71) Applicant: Biosense Webster (Israel) Ltd., Yokneam (IL)

(72) Inventors: Yehuda Algawi, Binyamina (IL); Assaf Govari, Haifa (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/423,214

(22) Filed: Feb. 2, 2017

(65) Prior Publication Data

US 2018/0214170 A1   Aug. 2, 2018

(51) Int. Cl.
| | |
|---|---|
| *A61B 17/32* | (2006.01) |
| *A61B 17/00* | (2006.01) |
| *A61B 17/24* | (2006.01) |
| *A61B 90/00* | (2016.01) |

(52) U.S. Cl.
CPC ........ *A61B 17/32002* (2013.01); *A61B 17/24* (2013.01); *A61B 2017/0023* (2013.01); *A61B 2017/0046* (2013.01); *A61B 2090/0813* (2016.02); *A61B 2217/005* (2013.01); *A61B 2217/007* (2013.01)

(58) Field of Classification Search
CPC ........ A61B 17/32002; A61B 2017/248; A61B 2017/246; A61B 2017/0023; A61B 17/24; A61B 2217/007; A61B 2217/005
See application file for complete search history.

(56) References Cited

U.S. PATENT DOCUMENTS

| | | | |
|---|---|---|---|
| 3,384,085 A | 5/1968 | Hall | |
| 4,986,825 A | 1/1991 | Bays et al. | |
| 5,437,630 A | 8/1995 | Daniel et al. | |
| 5,792,167 A | 8/1998 | Kablik et al. | |

(Continued)

FOREIGN PATENT DOCUMENTS

WO    02/094346 A1    11/2002

OTHER PUBLICATIONS

Communication pursuant to Article 94(3) EPC dated Aug. 14, 2019 for the European Patent Application No. 18154694.6.

(Continued)

*Primary Examiner* — Katrina M Stransky
(74) *Attorney, Agent, or Firm* — Volpe Koenig

(57) ABSTRACT

An extended blade of a surgical cutting instrument is provided. The blade may comprise a distal cutting end, a distal non-cutting end, and an intermediate portion that extends coaxially from the distal cutting end to the distal non-cutting end. The distal cutting end may be located outside of a housing of the instrument; the distal non-cutting end may be located at a posterior end of a suction portion inside the housing; and the intermediate portion may extend coaxially from the distal cutting portion, completely through a chamber portion of the housing, and to the suction portion to the distal cutting end. This configuration allows for biological material to be cut and aspirated completely through the disposable blade and housing to a suction source, avoiding contamination and improving instrument sterilization for surgeries.

15 Claims, 6 Drawing Sheets

(56) References Cited

U.S. PATENT DOCUMENTS

| | | |
|---|---|---|
| 2004/0059363 A1* | 3/2004 | Alvarez ........... A61B 17/32002 |
| | | 606/170 |
| 2004/0082915 A1 | 4/2004 | Kadan |
| 2005/0135776 A1* | 6/2005 | Vijfvinkel ...... A61B 17/320016 |
| | | 385/147 |
| 2007/0073326 A1 | 3/2007 | Miller et al. |
| 2010/0152762 A1 | 6/2010 | Mark |
| 2012/0078279 A1* | 3/2012 | Mark ................. A61B 10/0275 |
| | | 606/171 |
| 2013/0131706 A1 | 5/2013 | Flynn et al. |
| 2017/0172796 A1* | 6/2017 | Biancalana ........... A61M 39/24 |

OTHER PUBLICATIONS

Extended European Search Report dated Mar. 13, 2018 for the European Patent Application No. 18154694.6.

\* cited by examiner

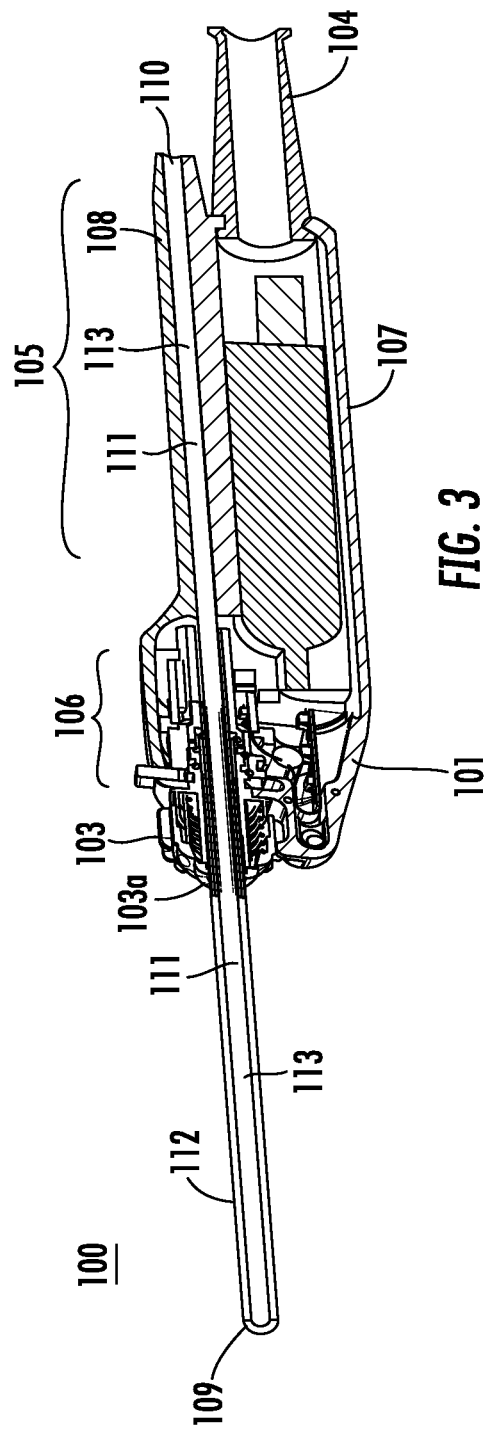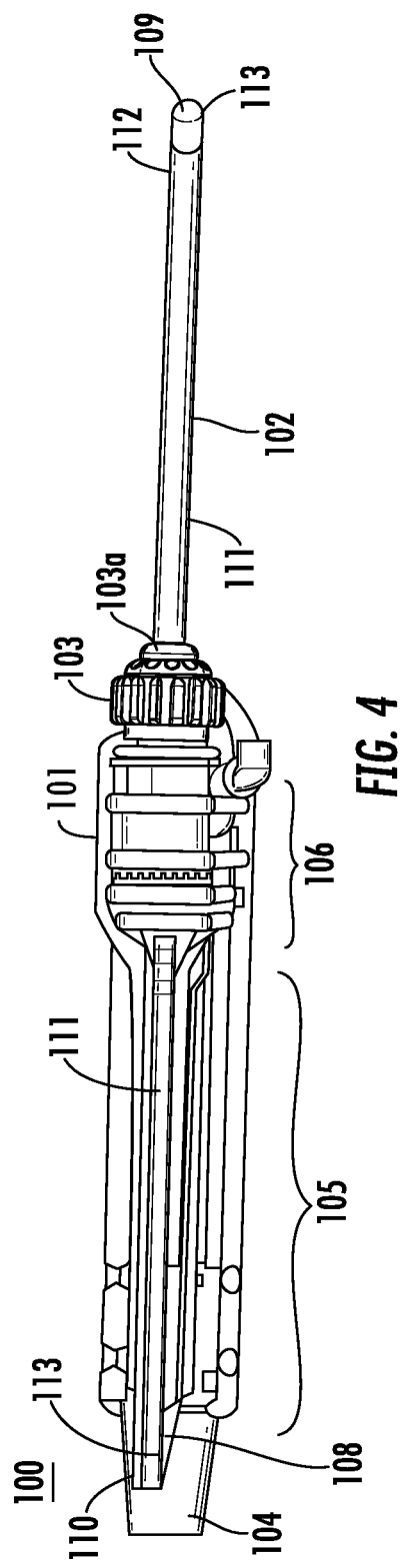

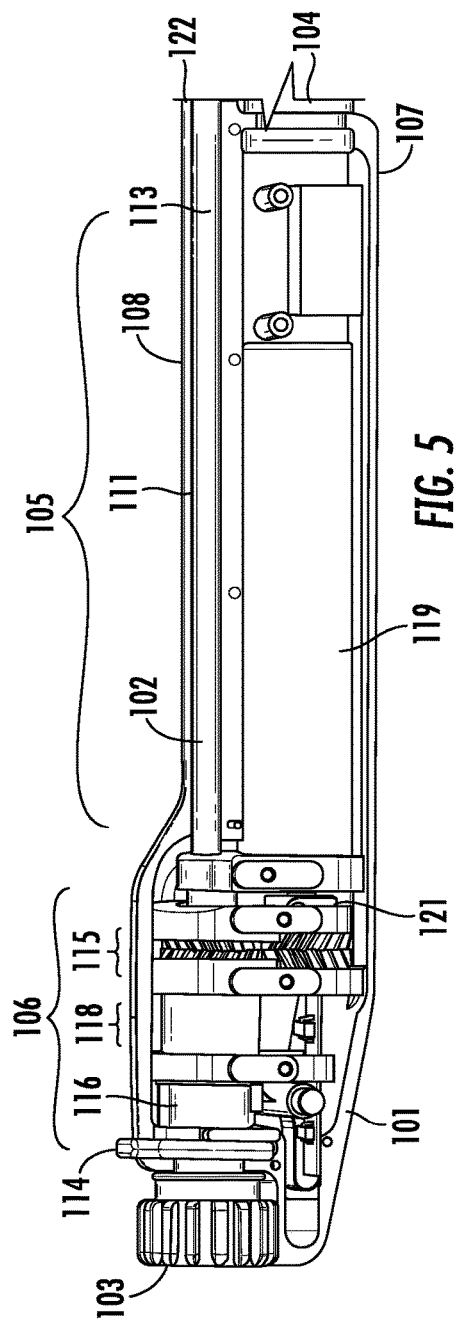
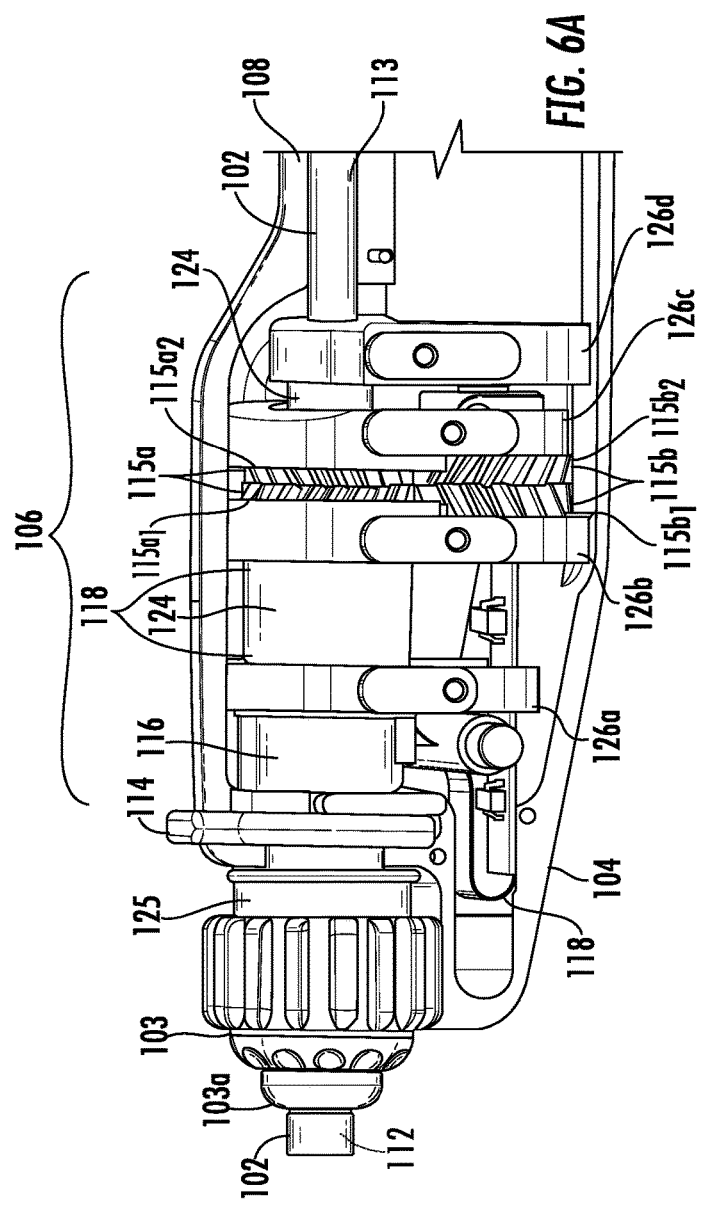

SURGICAL CUTTING INSTRUMENT WITH EXTENDED BLADES

FIELD OF INVENTION

The present invention relates generally to a surgical cutting instrument, and more specifically to a cutting instrument with an extended blade for ear, nose, and throat (ENT) surgery.

BACKGROUND

ENT surgery is the surgical treatment of diseases, injuries, or deformations of the ears, nose, throat, head, and neck areas. ENT surgery is one of the most elaborate fields of surgical specialty services, using advanced technology and a broad range of procedures that also includes major reconstructive surgery to correct deformity or injury. As a result, numerous surgical instruments, including a range of surgical cutting instruments, must be relied upon to successfully perform such procedures.

Current surgical cutting instruments are designed with a disposable blade portion, and non-disposable housing portion. The non-disposable housing portion typically includes a proximal chamber portion, a handpiece, and contains a suction passage, irrigation system, and motor mechanism to drive the disposable blade. The disposable blade portion comprises a short blade and is affixed to the distal end of the non-disposable housing portion of the instrument. Utilizing this configuration, biological material that is cut and suctioned from the body must pass through both the disposable blade and the non-disposable portion of the housing.

The diameter of the suction tubing is smaller than the diameter of the blade. To allow cut material to pass between the disposable blade and the non-disposable housing, the suction passage must be narrower to increase the suction into the narrow tubing. Thus, as cut biological material is aspirated, clogging and backup can occur in the suction passage of the non-disposable housing. The sterilization process for the housing is therefore tedious, since one or more specialized brushes are required to scrub the inside of the non-disposable housing free of biological material to properly sterilize the housing portion. This complexity of the sterilization process can therefore lead to incomplete sterilization of the instrument.

It would therefore be useful to offer a surgical cutting instrument that prevents biological material from being trapped in the non-disposable portion of the instrument and allows for a more thorough sterilization.

SUMMARY

A blade for use in a surgical cutting instrument comprising a distal cutting end, a distal non-cutting end, and an intermediate portion. The surgical cutting instrument comprises a housing that includes a chamber portion and a suction portion. The intermediate portion extends coaxially from the distal cutting end, into the housing, passes through the chamber portion, and extends coaxially into the suction portion to the distal non-cutting end. Thus, the distal cutting end may be located at an end of a part of the blade that protrudes from the housing, the distal non-cutting end may be located at a posterior end of the suction portion, and the intermediate portion may extend coaxially from the distal cutting portion, completely through the chamber portion of the housing, and to the suction portion.

The blade may be a rigid, circular tube with constant diameter, and may be disposable. The blade may further comprise an outer member, and an inner member. The outer member may extend from the distal cutting end to a portion of the blade outside of the housing. The inner member may extend from the distal cutting end, into the housing, pass through the chamber portion, and extend coaxially into the suction portion to the distal non-cutting end. This configuration may allow for biological material to be cut and aspirated completely through the blade and housing to a suction source, avoiding contamination and improving instrument sterilization for surgeries.

The blade may coaxially pass through components of the chamber portion that are coupled coaxially. These components may include a gear train, an irrigation system, and a flexible printed circuit board, and a blade locking mechanism. The blade locking mechanism may fix the blade in the housing during operation. The suction portion may contain the distal non-cutting end of the blade. The distal non-cutting end of the blade may extend to any point inside the suction portion, including up to a posterior end of the suction portion. Thus, as biological material is cut during surgery, the material may be irrigated with fluid and suctioned through the entirety of the blade to the suction portion, and ultimately through suction tubing to a suction source, while avoiding being trapped in the non-disposable housing.

BRIEF DESCRIPTION OF THE DRAWINGS

The present invention is illustrated by way of example, and not by way of limitation, in the figures of the accompanying drawings in which:

FIG. 3 is a diagram of a cross-sectional perspective view of the surgical cutting instrument.

FIG. 4 is a diagram of a plan view of the surgical cutting instrument and contents of the housing.

FIG. 5 is a diagram of a side view of the contents of an anterior chamber portion, base portion, and suction portion of a housing of the surgical cutting instrument.

FIG. 6A is a diagram of a side view of an anterior chamber portion of a housing of the surgical cutting instrument.

DETAILED DESCRIPTION OF THE PREFERRED EMBODIMENTS

A surgical cutting instrument may be configured such that the cutting disposable blades pass completely through the handle. This configuration may permit easier and more thorough sterilization of the tool handle, since all of the cut tissue may be discarded in the disposable portion. In addition, extending the blade may simplify the sterilization process and make adherence to proper sterilization procedures much more likely.

Figure 1:
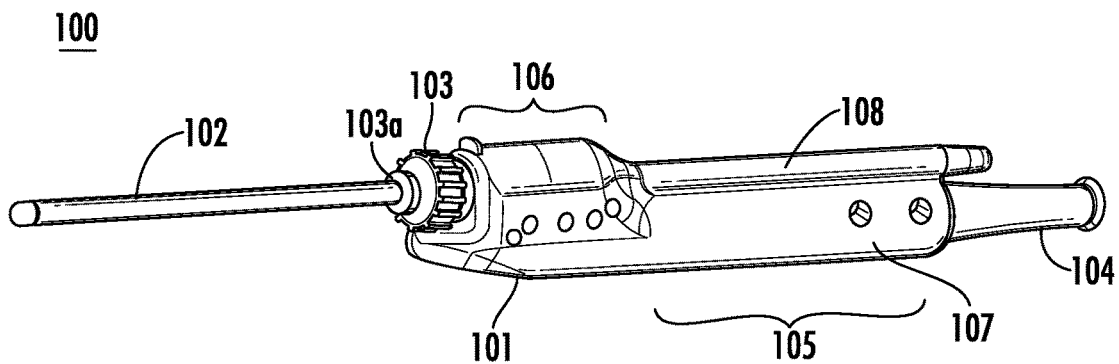
FIG. 1 is a diagram of a perspective view of the surgical cutting instrument.

FIG. 1 is a diagram of a perspective view of the surgical cutting instrument 100. Surgical cutting instrument 100 comprises a housing 101, a blade 102, an outer position knob 103, and a power cord housing 104. The outer position knob 103 comprises an opening 103a to allow the blade 102 to pass through the outer position knob 103. Blade 102 is fixed in the housing 101 and extends coaxially through the outer position knob 103 via opening 103a. The housing 101 comprises a posterior handpiece portion 105 and an anterior chamber portion 106. The posterior handpiece portion 105 includes a base portion 107 and a suction portion 108. In this embodiment, the suction portion 108 is located above base portion 107. The suction portion 108 may, however, be located below or anywhere around the base portion 107 inside the handpiece portion 105. Suction portion 108 may be connected on its posterior end to a suction source via a suction tube (not depicted). The blade 102 extends through the housing 101, through the anterior chamber portion 106, and to a suction portion 108. The blade 102 may extend to a posterior end of the suction portion 108.

Figure 2:
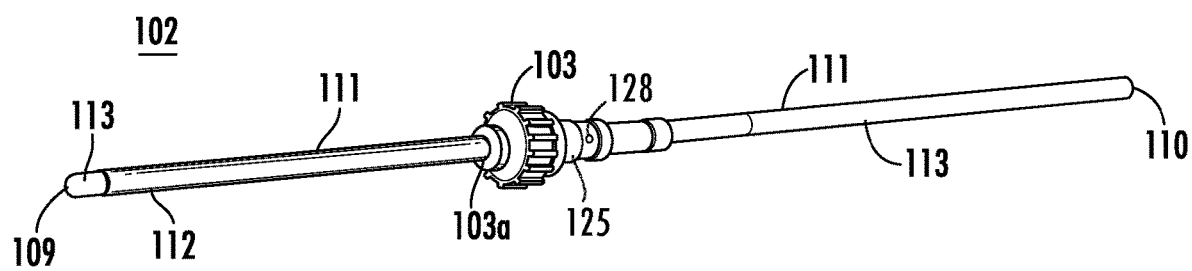
FIG. 2 is a diagram of a perspective view of a blade of the surgical cutting instrument.

FIG. 2 is a diagram of a perspective view of a blade 102 of the surgical cutting instrument. The blade 102 may be a rigid, hollow circular tube with a constant diameter of 2.0-6.0 millimeters (mm). The blade 102 may also be 200-300 mm in length. The blade 102 may be made of stainless steel, titanium, or other metal alloy and may be disposable. In this example embodiment, blade 102 comprises a distal cutting end 109, a distal non-cutting end 110, and an intermediate portion 111 extending from distal cutting end 109, to distal non-cutting end 110. Thus, intermediate portion 111 may extend through the entire length of the housing to the distal non-cutting end 110. Both the distal cutting end 109 and the distal non-cutting end 110 may be open; and the distal non-cutting end 110 may extend to the posterior end of the suction portion 108 (as depicted in FIG. 1) to further allow fluid and debris to pass through the blade and aspirated.

Blade 102 includes an outer member 112 and an inner member 113. Outer member 112 coaxially extends from the distal cutting end 109, through the opening 103a, to a section of the intermediate portion 111 located outside of the housing 101. Inner member 113 coaxially extends from the distal cutting end 109, through the opening 103a, through the housing, and to the distal non-cutting end 110.

Tissue and other biological material are cut at the distal cutting end 109 and pass through the entirety of the blade, through the housing 101, and all the way through the distal non-cutting end 110. The distal cutting end 109 also includes the outer member 112 and the inner member 113. The inner member 113 may extend from the distal cutting end 109, all the way back to the distal non-cutting end 110. The outer member 112 may extend from the distal cutting end 109, to a section of the intermediate portion 111 outside of the housing 101. Both the outer member 112 and the inner member 113 include openings at the distal cutting end 109. The opening of the outer member 112 at the distal cutting end 109 may be located on a top side of the outer member 112 and may be surrounded by a set of teeth (not depicted) to allow for tissue to be cut and passed through the opening. The opening of the outer member 112 at the distal cutting end 109 may expose a portion of the inner member 113. The opening of the inner member 113 at the distal cutting end 109 may be located on a bottom side of the inner member 113 and may also be surrounded by a set of teeth (not depicted) to allow for tissue to be cut and passed through the opening. The outer member 112 may surround the opening of the inner member 113 completely.

The blade 102 may have a hole 128 for irrigation and aspiration of cut biological material. The hole 128 may be located on an inner knob 125 to allow for saline or other liquid to pass through the outer member 112, to a suction site (not depicted), and up through the inner member 113 to the distal non-cutting end 110 during irrigation and aspiration.

FIG. 3 is a diagram of a cross-sectional perspective view of the surgical cutting instrument 100. The blade 102 may extend through the housing 101. The distal non-cutting end 110 is located in housing 101 and the distal cutting end 109 is located at the end of a part of the blade that protrudes from the housing 101. The intermediate portion 111 of the blade 102 coaxially extends from the distal cutting end and passes through the outer position knob 103 via opening 103a and further extends through the housing 101 to the distal non-cutting end 110 in the suction portion 108.

The outer member 112 may extend from the distal cutting end 109 through an opening 103a to a section of the intermediate portion 111 just before the intermediate portion 111 enters the housing 101. The inner member 113 extends from the distal cutting end 109, completely through the anterior chamber portion 106, to the distal non-cutting end 110 located in the suction portion 108. The distal non-cutting end 110 may have a variable length and may extend to any location inside suction portion 108, including up to a back end of suction portion 108. Thus, the blade 102 may extend through and to the back end of the handpiece 105 and, consequently, to the back of the housing 101, all the way to the end of the suction portion 108.

FIG. 4 is a diagram of a plan view of the surgical cutting instrument 100 and contents of the housing 101. The blade 102 extends through the outer position knob 103 via the opening 103a, through the anterior chamber portion 106, and to the back end of the suction portion 108. The blade 102 coaxially extends and passes through the housing 101. Inner member 113 of the blade 102 extends into the suction portion 108, and may extend to a posterior end of the suction portion 108.

Surgical cutting instruments are currently designed with a shorter disposable blade and a non-disposable housing. In surgical procedures using current surgical cutting instruments, biological material cut and suctioned from the body must pass through both the disposable blade and the non-disposable housing. Suction tubing is typically narrower in diameter to allow the cut material to pass between the disposable and non-disposable portions of the cutting instrument. As a result, cut biological material may clog the tubing and may also become lodged between the disposable blade and non-disposable housing. With current blades, the blade typically extends into the housing only up to, and not past, a proximal chamber of the housing. By having the blade portion stop at a proximal chamber of the housing, contamination of the handpiece is increased and sterilization becomes difficult.

Returning to FIG. 4, the blade 102 extends into the housing 101, completely through the anterior chamber portion 106, to the suction portion 108. In one embodiment, the blade 102 may extend to the back end of the suction portion 108. This configuration allows for an increased suction tube diameter which, in turn, increases the flow of biological material through the suction tube. Thus, clogging of biological material in the tubing may be avoided such that the biological material would not have to pass through both the disposable blade and non-disposable housing.

Instead, when tissue or biological material is cut or comminuted by the blade 102, the debris may be suctioned through the entirety of the blade 102, which extends completely through the anterior chamber portion 106 and to the end of the suction portion 108. The debris may then pass through a suction tube into a suction source. Thus, the debris does not come in contact with the components of the housing 101 as it does in typical surgical cutting instruments. As a result, easier and more thorough sterilization and avoidance of contamination of the surgical cutting instrument 100 can be achieved.

The blade 102 may also be retrofitted to pass through the non-disposable housing of current surgical cutting instruments, provided that the housing components are coaxially coupled to accommodate an extended blade. In the present embodiment, the configuration of the components inside the anterior chamber portion 106 is coaxially coupled to accommodate the blade 102 extending and passing through the entirety of the anterior chamber portion 106. This enables the blade 102 to pass completely through the components of the anterior chamber portion 106 into the suction portion 108, allowing for more thorough sterilization of the housing by having the cut biological material pass completely through the blade 102 into the suction passage 108.

FIG. 5 is a diagram of a side view of the contents of the anterior chamber portion 106, base portion 107, and suction portion 108 of a housing 101 of the surgical cutting instrument 100. The blade 102 coaxially passes and extends through the anterior chamber portion 106, and to a suction portion 108. The blade 102 may extend all the way to a posterior end of the suction portion 108.

Housing packaging of current surgical cutting instruments may be cramped to include a short blade, a suction passage system, an irrigation system, and a motor mechanism to drive the blade. The suction portion and suction tubing are therefore narrower to accommodate the shortened blade. As a result, cut biological material can clog in the non-disposable housing when being suctioned. Current blades, however, do not alleviate cramped packaging of the components or narrow suction diameters because the blades typically extend into the housing only up to and not past the proximal chamber of the housing. By having the blade portion stop at the proximal chamber of the housing, sterilization becomes increasingly difficult because the material can clog in the non-disposable housing.

Referring to FIG. 5, the blade 102 extends into the housing 101, completely through the anterior chamber portion 106 to the suction portion 108, and passes coaxially through the components located in the anterior chamber portion 106. This configuration allows for the blade 102 to pass through the components of the anterior chamber portion 106. As a result, easier sterilization can be achieved because the cut biological material is passing completely through the blade 102 to the suction portion 108.

The anterior chamber portion 106 is a hollow portion of the housing 101 that may include a blade locking mechanism 114, a gear train 115, an irrigation system 116, an irrigation valve 117 on its outer surface (not depicted), and a flexible printed circuit board 118. The base portion 107 is a hollow portion of the housing 101 that may include a motor mechanism 119 and the flexible printed circuit board 118. The motor mechanism 119 may include a rotary output shaft 121 extending forward from the mechanism that drives the gear train 115. The suction portion 108 is a hollow portion of the housing 101 that contains the inner member 113 of the blade 102. The suction portion may have a diameter dimensions large enough to allow the blade 102 to pass through, and may have a thickness of 0.1-1.0 mm. The suction portion 108 may include a suction valve 122 at its posterior end. The suction valve 122 may be attached to a suction tube and suction source (not depicted) for aspiration of cut biological material. In one embodiment, the inner member 113 of the blade 102 may extend all the way to the end of the suction valve 122. Thus, biological material may be suctioned through the entirety of the blade in the housing and directly into a suction tube and suction source.

FIG. 6A is a diagram of a side view of the anterior chamber portion 106 of a housing 101 of the surgical cutting instrument 100. The blade 102 coaxially extends and passes through the anterior chamber portion 106. The inner member 113 of the blade 102 extends into the suction portion 108. The blade 102 may be retrofitted into current surgical cutting tools provided that the housing components are coaxially coupled to accommodate an extended blade. In the present embodiment, the configuration of the components inside the anterior chamber portion 106 is coaxially coupled to accommodate the blade 102 extending and passing through the entirety of the anterior chamber portion 106. This enables the blade 102 to pass completely through the components of the anterior chamber portion 106 into the suction portion 108, allowing for more thorough sterilization of the housing by having the cut biological material pass completely through the blade 102 into the suction passage 108.

The gear train 115 is located at a posterior end of anterior chamber portion 106. The gear train 115 may include an upper gear set 115a and a lower gear set 115b. The upper gear set 115a may include a helical gear $115a_1$ and a helical gear $115a_2$ coupled coaxially. The lower gear set 115b may also include a helical gear $115b_1$ and a helical gear $115b_2$ coupled coaxially. Other types of gears may be used in the gear train 115, including spur or V gears. Thus, the teeth of the helical gears $115a_1$ and $115a_2$ may engage with each other while the teeth of the helical gears $115b_1$ and $115b_2$ engage with each other when the gears are rotating. The gear train 115 may be welded to the inner member 113 of the blade 102 to drive the blade 102. Thus, rotation of the gear train 115 drives the blade 102 to move and cut biological material.

In the present embodiment, the helical gear $115a_1$ is coaxially coupled to an flexible printed circuit board housing 123. The flexible printed circuit board housing 123 is coaxially coupled to the irrigation system 116. The helical gear $115a_2$ is coaxially coupled to an outer hollow casing 124 that makes up the flexible printed circuit board 118. The irrigation system 116 is coupled to locking mechanism 114. The irrigation system 116 and the locking mechanism 114 coaxially surround an inner knob 125. The inner knob 125 is coaxially coupled to the outer position knob 103.

The irrigation system 116 and the flexible printed circuit board housing 123 may be further coupled to each other and held in place via a spacer 126a. Spacer 126a may also couple the irrigation system 116 and the flexible printed circuit board housing 123 to the flexible printed circuit board 118 on parallel axes. The flexible printed circuit board housing 123 and helical gear $115a_1$ may be further coupled to each other and held in place via a spacer 126b. Spacer 126b may further couple the flexible printed circuit board housing 123 and helical gear $115a_1$ to helical gear $115b_1$ on parallel axes. Helical gear $115a_2$ and outer hollow casing 124 may be further coupled to each other and held in place via a spacer 126c. Spacer 126c may further couple helical gear $115a_2$ to helical gear $115b_2$ on parallel axes. The outer hollow casing 124 and the motor mechanism 131 may be further coupled to each other on parallel axes via a spacer 126d. In other embodiments, the components may be coupled on parallel axes via any other coupling means.

Thus, in this configuration, when the blade 102 is inserted into the housing 101, it coaxially passes and extends through the outer position knob 103 via the opening 103a, and extends completely through the anterior chamber portion 106 by passing coaxially through the inner knob 125, the locking mechanism 114, the irrigation system 116, spacer 126a, the flexible printed circuit board housing 123, spacer 126b, the upper gear set 115a, spacer 126c, the outer hollow casing 124, and spacer 126d; and then extends into the suction portion 108. Having the blade 102 extend completely through the anterior chamber portion 106 and coaxially through the components of the anterior chamber portion 106, instead of stopping the blade inside the chamber portion in current surgical cutting instruments, allows for cut biological material to be suctioned and pass completely through the blade 102 into the suction portion 108 to improve sterilization by avoiding contamination in the anterior chamber portion 106.

Figure 6B:
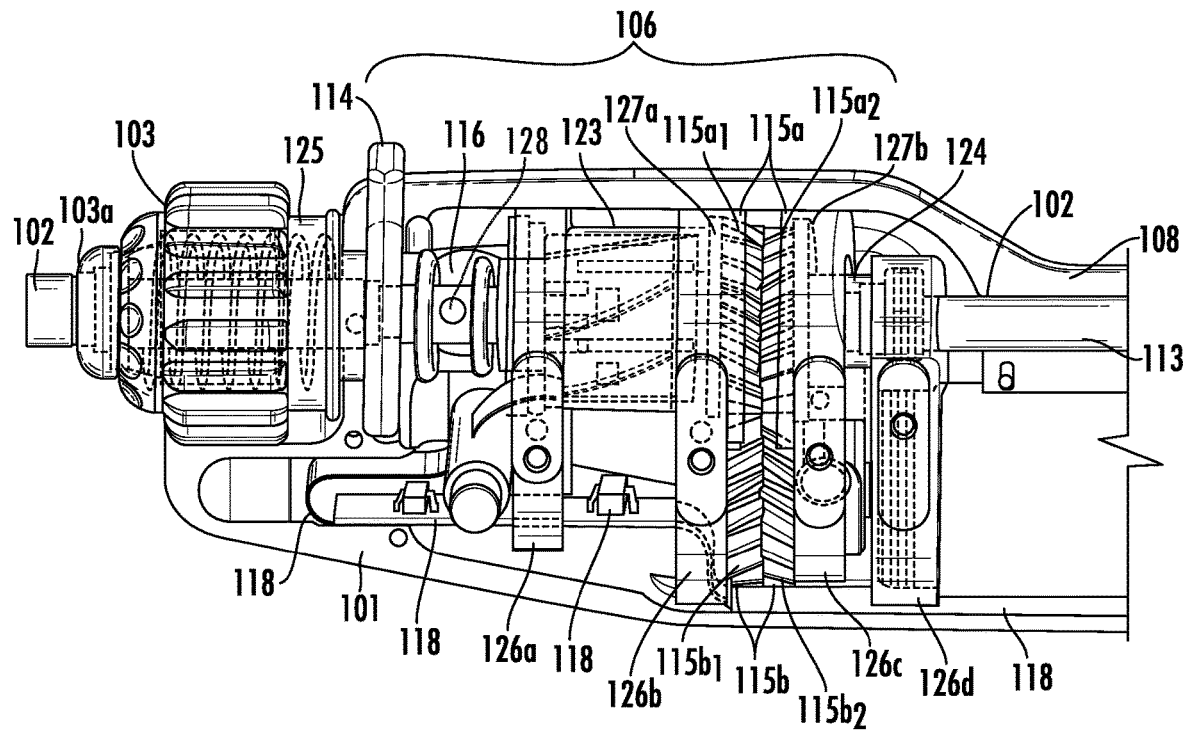
FIG. 6B is a diagram of a side view of inner contents of an anterior chamber portion of a housing of the surgical cutting instrument.

FIG. 6B is a diagram of inner contents of an example chamber portion 106 and flexible printed circuit board 118 of the surgical cutting instrument. The blade 102 coaxially extends and passes through the inner contents of the chamber portion 106 and flexible printed circuit board 118, through the anterior chamber portion 106, and into the suction portion 108. Flexible printed circuit board 118 includes flexible printed circuit board housing 123. Helical gear $115a_1$ may be further coaxially coupled to a washer 127a, which in turn may be further coaxially coupled to the flexible printed circuit board housing 123. Helical gear $115a_2$ may also be further coaxially coupled to a washer 127b, which in turn may be further coaxially coupled to the outer hollow casing 124. The flexible printed circuit board housing 123 may surround the flexible printed circuit board 118 and may be further coaxially coupled to the irrigation system 116.

Washer 127a and helical gear $115a_1$ may be further coupled to each other and held in place via spacer 126b. Spacer 126b may further couple washer 127a and helical gear $115a_1$ to helical gear $115b_1$ on parallel axes. Helical gear $115a_2$ and washer 127b may be further coupled to each other and held in place via spacer 126c, which may further couple washer 127b and helical gear $115a_2$ to helical gear $115b_2$ on parallel axes. The outer diameter of the washers and spacers may be 6.0-7.0 mm. The inner diameter of the washers and spacers may be 3.0-4.0 mm. In other embodiments, the components may be coaxially coupled and coupled on parallel axes via any other coupling means.

The inner knob 125 also includes a hole 128, which is surrounded by the irrigation system 116. The hole 128 allows saline or other liquid to pass from the irrigation system 116 to the blade 102, in order to aid in aspiration of cut biological material as it passes through the extended blade 102 to a suction portion 108. In this configuration, when the blade 102 is inserted into the housing 101, it coaxially extends and passes through the outer position knob 103 via the opening 103a, the inner knob 125, the locking mechanism 114, the irrigation hub 126, spacer 126a, flexible printed circuit board 118, and the flexible printed circuit board housing 123, spacer 126b, washer 127a, helical gears $115a_1$ and $115a_2$, spacer 126c, washer 127b, the outer hollow casing 124, and spacer 126d, and then extends into the suction portion 108. The coaxial coupling of the components in the anterior chamber portion 106 allow for the blade 102 to pass through the components of the anterior chamber portion 106 to the suction portion 108.

The hole 128 on the inner knob 125 is surrounded by the irrigation system 116. Once the blade 102 is inserted, the hole 128 on the inner knob 125 aligns with the irrigation system 116 such that fluid flows from the irrigation system 116 into the hole 128 and subsequently into the blade 102. Thus, cut biological material as well as liquid passes right through the anterior chamber portion 106 inside the blade 102 to the suction portion 108, providing an easier and more thorough sterilization as the blade extends through the components of the chamber.

Figure 7A:
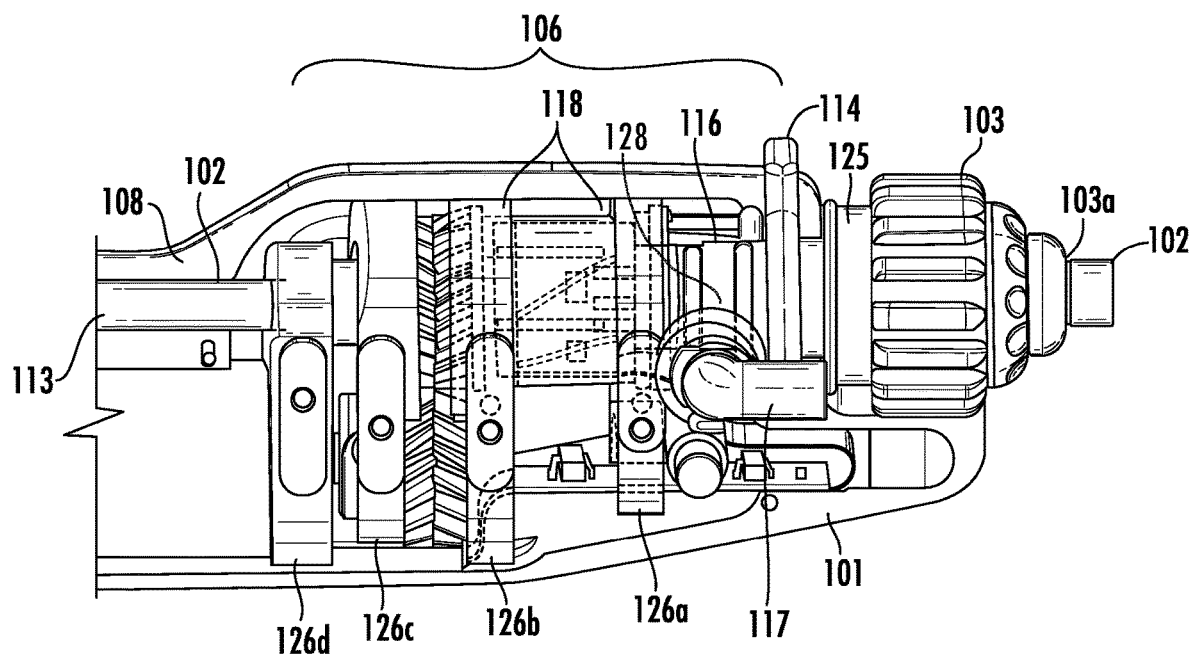
FIG. 7A is a diagram of a side view of an irrigation valve and irrigation system in an anterior chamber portion of a housing of the surgical cutting instrument.

FIG. 7A is a diagram of an example irrigation system 116 and irrigation valve 117 in an anterior chamber portion 106. The blade 102 coaxially extends and passes through the irrigation system 116. The irrigation valve 117 allows liquid to flow directly into the blade 102, and pass through the blade 102 as the blade 102 extends through the irrigation system 116, through the anterior chamber portion 106, and into the suction portion 108.

In various surgical procedures, it is desirable to irrigate the surgical site with liquid and then draw by suction the irrigation liquid and biological material from the surgical site. To achieve this, irrigation tubing connected to an irrigation source (not depicted) may be connected to the irrigation valve 117. Saline or any other liquid suitable for performing irrigation may then pass through the irrigation valve 117 through the irrigation system 116, and subsequently through the hole 128 on inner knob 125.

When the blade 102 is inserted into the housing, the hole 128 on the inner knob 125 aligns with the irrigation system 116 such that the irrigation system 116 surrounds and contains the hole 128 on the inner knob 125. Fluid then flows from the irrigation valve 117, into the irrigation system 116, into the hole 128 and subsequently into the blade 102. The hole 128 allows the liquid to pass through the outer member 112 of the blade 102 to the surgical site, and eventually through the inner member 113 of the blade 102 as it is aspirated with cut biological material. The liquid flows radially through the entirety of the inner member 113 of the blade 102 via suction as the blade 102 extends to a suction portion 108, and then outward into a suction tube. Thus, the surgical cutting instrument 100 can be used for simultaneously cutting tissue at the surgical site and removing flowable material from the surgical site through the extended blade 102.

Figure 7B:
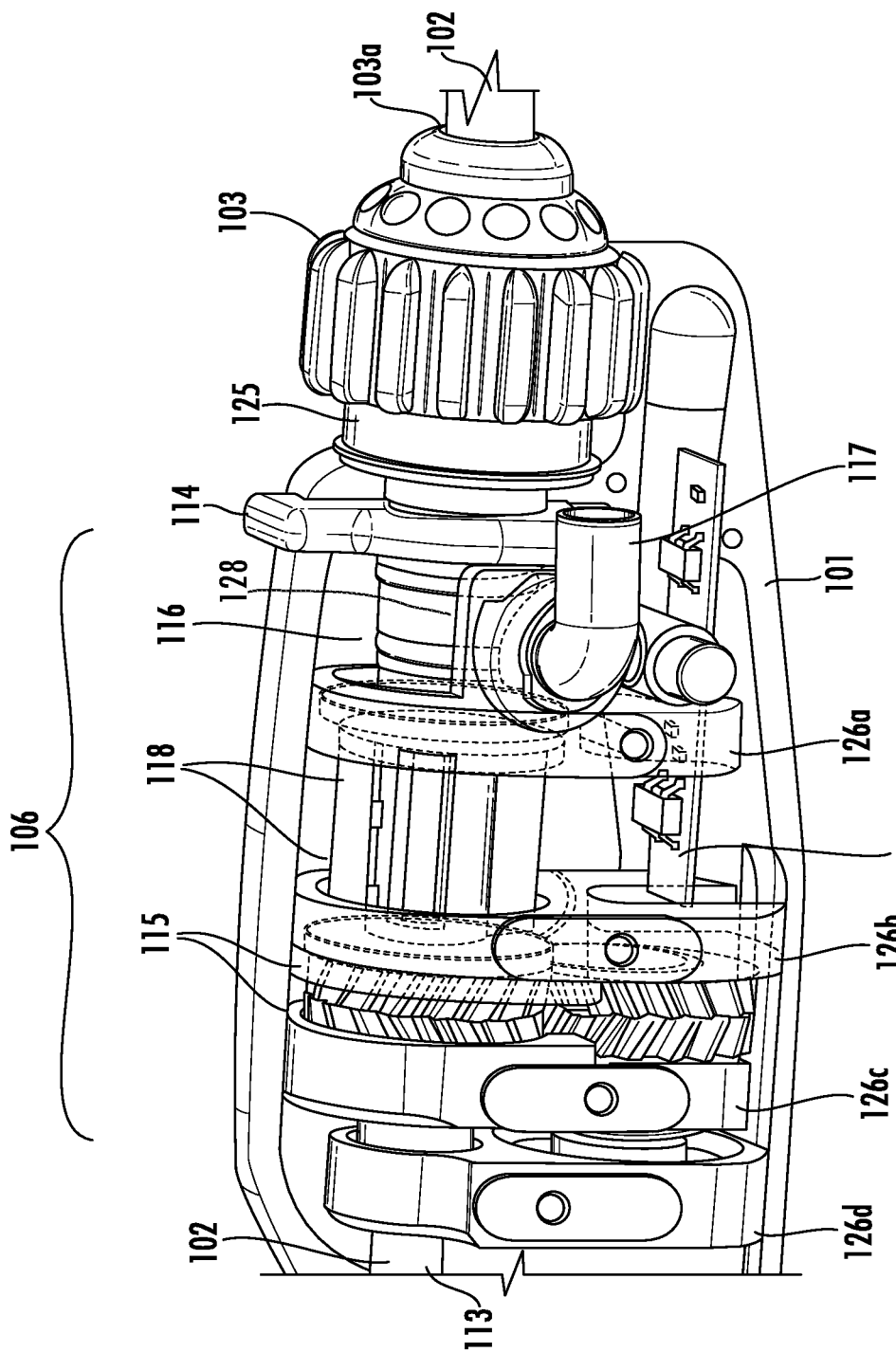
FIG. 7B is a diagram of a side view of inner contents of an irrigation valve and irrigation system in an anterior chamber portion of a housing of the surgical instrument.

FIG. 7B is a diagram of inner contents of an example irrigation system 116 and flexible printed circuit board 118 in an anterior chamber portion 106. The blade 102 coaxially extends and passes through the irrigation system 116 and printed circuit board 118, and further through the anterior chamber portion 106. The inner member 113 of the blade 102 extends into the suction portion 108 (as shown in FIG. 7A). During irrigation, liquid enters the irrigation system 116. The irrigation system 116 surrounds and contains the hole 128 on the inner knob 125. Thus, once the blade 102 is inserted, the hole 128 on the inner knob 125 aligns with the irrigation system 116 such that fluid flows from the irrigation system 116 into the hole 128 and subsequently into the blade 102. Liquid subsequently enters the outer member 112 of the blade 102 through the hole 128 on inner knob 125. The liquid then flows to the surgical site and eventually flows radially through the entirety of the inner member 113 of the blade 102 as it extends to the suction portion 108 via suction. The liquid is then suctioned through the inner member 113 as it passes through the suction portion 108 (as shown in FIG. 7A). Current surgical cutting instrument blades are not configured to allow fluid to flow from an irrigation valve, into an irrigation system, through a hole in an inner knob, into an outer member, and through an inner member of the blade as it extends to a suction portion during aspiration.

Thus, having the inner member 113 of the blade 102 extend completely through the anterior chamber portion 106 and coaxially through the components of the anterior chamber portion 106, instead of stopping the blade inside the chamber portion in current surgical cutting instruments, and having the hole 128 on the inner knob 125 allows for liquid to flow radially throughout the blade to the surgical site and then be aspirated along with cut biological material. The biological material and liquid can be suctioned and passed completely through the blade 102 into the suction portion 108 to improve sterilization by avoiding contamination in the anterior chamber portion 106.

Figure 8:
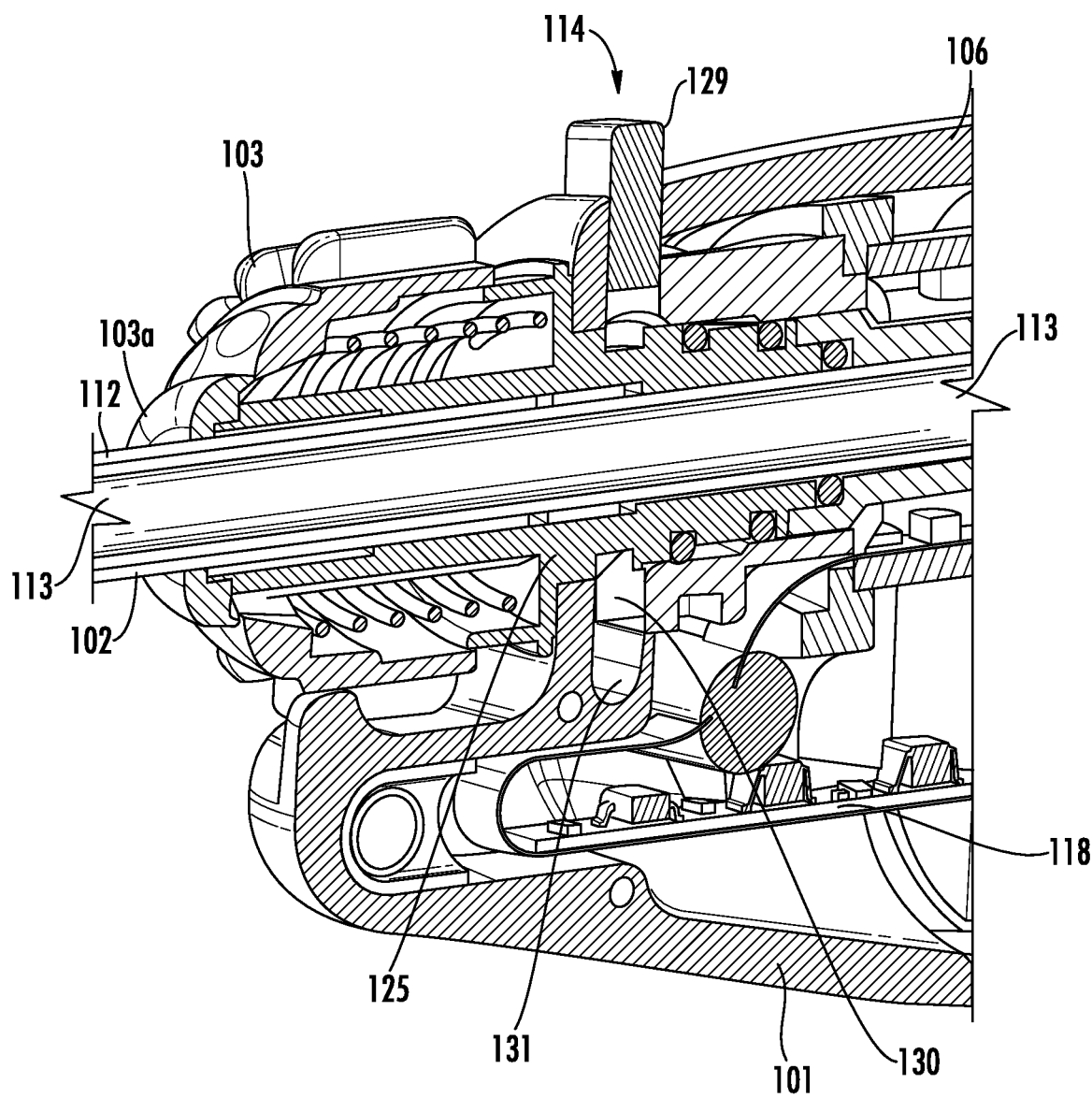
FIG. 8 is a diagram of a cross-sectional perspective view of a blade locking mechanism of the surgical cutting instrument.

FIG. 8 depicts the blade 102 as the inner member 113 is locked in the anterior chamber portion 106 of the housing 101. The blade 102 coaxially extends and passes through the blade locking mechanism 114. The blade 102 may be locked in place in the housing 101 by the blade locking mechanism 114. The blade locking mechanism 114 may be made of a polymeric material and may be located at an anterior end of the anterior chamber portion 106. The blade locking mechanism 114 comprises a push button 129, a locking tooth 130, and a spring 131. Pressing and holding the push button 129 pushes the locking tooth 130 and the spring 131 in a downward direction away from the blade 102. Thus, when the push button 129 is pressed downward and held, the blade 102 can be inserted into the housing 101. Releasing the push button 129 releases the spring 131 and pushes the locking tooth 130 in an upward direction and against the inner knob 125 and further against the blade 102, thus locking the blade 102 in place. Pressing and holding the push button 129 subsequently releases the blade 102 for disposal.

It should be understood that many variations are possible based on the disclosure herein. Although features and elements are described above in particular combinations, each feature or element can be used alone without the other features and elements or in various combinations with or without other features and elements.

What is claimed is:

1. A blade of a surgical cutting instrument comprising:
a distal cutting end;
an intermediate portion operatively coupled to the distal cutting end; and
a distal non-cutting end operatively coupled to the intermediate portion,
wherein the intermediate portion extends through an entire length of a housing of the surgical cutting instrument, the housing having an anterior portion and a posterior handpiece portion,
wherein the posterior handpiece portion includes a base portion and a suction portion and each of the base portion and the suction portion comprises a respective hollow portion of the housing;
wherein the distal non-cutting end coaxially extends from the intermediate portion to the posterior handpiece portion of the housing of the surgical cutting instrument, and
wherein the suction portion is operatively coupled in a continuous connection to a suction tube disposed outside of the housing.

2. The blade of claim 1, wherein the blade is a rigid, hollow circular tube with constant diameter.

3. The blade of claim 1, wherein the blade further comprises:
an outer member, and
an inner member.

4. The blade of claim 3, wherein the outer member is configured to extend from the distal cutting end to a portion of the blade outside of the surgical cutting instrument.

5. The blade of claim 3, wherein the inner member extends coaxially from the distal cutting end, through the surgical cutting instrument, and into the suction portion of the distal non-cutting end.

6. The blade of claim 3, wherein the inner member extends coaxially and passes through components of the surgical cutting instrument coupled coaxially, to the suction portion.

7. The blade of claim 6, wherein the components include a blade locking mechanism, a gear train, an irrigation system, and a flexible printed circuit board that are coaxially coupled in the surgical cutting instrument.

8. The blade of claim 7, wherein the irrigation system surrounds a hole on the blade to allow liquid to pass from the irrigation system to the blade and to a surgical site.

9. The blade of claim 8, wherein the blade allows liquid to pass from the irrigation system, into the hole, through the outer member, to the surgical site, and further through the inner member to the suction portion of the distal non-cutting end.

10. The blade of claim 7, wherein the blade is fixed in the surgical cutting instrument by the blade locking mechanism at the intermediate portion.

11. The blade of claim 1, wherein the blade is inserted through an opening into the surgical cutting instrument.

12. The blade of claim 1, wherein the blade is configured to:
cut biological material, and
pass the cut biological material from the distal cutting end, through the intermediate portion which extends coaxially into the surgical cutting instrument and through the surgical cutting instrument, to the suction portion of the distal non-cutting end, and to a suction source via aspiration.

13. The blade of claim 1, wherein the blade is made of a metal alloy.

14. The blade of claim 1, wherein the blade is disposable.

15. A surgical cutting instrument, comprising: a housing including an anterior portion and a posterior handpiece portion, the posterior handpiece portion including a base portion and a suction portion, each of the base portion and the suction portion comprising a respective hollow portion of the housing; and
a blade comprising:
a distal cutting end;
an intermediate portion operatively coupled to the distal cutting end; and
a distal non-cutting end operatively coupled to the intermediate portion,
wherein the intermediate portion extends through an entire length of the housing of the surgical cutting instrument,
wherein the distal non-cutting end coaxially extends from the intermediate portion to the posterior handpiece portion of the housing of the surgical cutting instrument, and
wherein the suction portion is operatively coupled in a continuous connection to a suction tube disposed outside of the housing.

* * * * *

UNITED STATES PATENT AND TRADEMARK OFFICE
CERTIFICATE OF CORRECTION

PATENT NO. : 10,874,416 B2
APPLICATION NO. : 15/423214
DATED : December 29, 2020
INVENTOR(S) : Yehuda Algawi et al.

It is certified that error appears in the above-identified patent and that said Letters Patent is hereby corrected as shown below:

In the Specification

In Column 2, Line 1, delete "constant" and insert -- a constant --, therefor.
In Column 2, Line 47, delete "of" and insert -- of the --, therefor.
In Column 2, Line 53, delete "of" and insert -- of the --, therefor.
In Column 5, Line 24, delete "suction passage 108." and insert -- suction portion 108. --, therefor.
In Column 6, Line 26, delete "suction passage 108." and insert -- suction portion 108. --, therefor.
In Column 6, Line 43, delete "an flexible" and insert -- a flexible --, therefor.
In Column 7, Line 21, delete "of" and insert -- of the --, therefor.
In Column 8, Line 45, delete "of" and insert -- of the --, therefor.

In the Claims

In Column 9, Line 58, in Claim 1, delete "housing;" and insert -- housing, --, therefor.
In Column 10, Line 50, in Claim 15, delete "housing; and" and insert -- housing; --, therefor.

Signed and Sealed this
Eighth Day of November, 2022

*Katherine Kelly Vidal*

Katherine Kelly Vidal
*Director of the United States Patent and Trademark Office*